United States Patent [19]

Igaki et al.

[11] 4,074,973

[45] Feb. 21, 1978

[54] METHOD AND APPARATUS FOR DETERMINING TOTAL OXYGEN DEMAND OF COMBUSTIBLE MATERIALS IN AQUEOUS DISPERSION

[75] Inventors: Hiroyuki Igaki; Yoshiki Shibata; Masao Saruyama, all of Otsu, Japan

[73] Assignee: Toray Industries, Inc., Tokyo, Japan

[21] Appl. No.: 669,272

[22] Filed: Mar. 22, 1976

Related U.S. Application Data

[63] Continuation of Ser. No. 638,361, Feb. 8, 1975.

[51] Int. Cl.$^2$ ............................................. G01N 31/12
[52] U.S. Cl. ............................ 23/230 PC; 23/253 PC
[58] Field of Search ...................... 23/230 PC, 253 PC

[56] References Cited

U.S. PATENT DOCUMENTS

| | | | |
|---|---|---|---|
| 3,428,432 | 2/1969 | Staunton et al. | 23/253 PC X |
| 3,560,156 | 2/1971 | Teal et al. | 23/230 PC |
| 3,565,583 | 2/1971 | McNulty et al. | 23/230 PC |
| 3,933,429 | 1/1971 | Shibata et al. | 23/230 PC |

*Primary Examiner*—Robert M. Reese
*Attorney, Agent, or Firm*—Miller & Prestia

[57] ABSTRACT

Means are provided for determining the TOD (total oxygen demand) of combustible materials contained in water, principally, sea water.

Test water containing halides of alkali metals or alkaline earth metals, such as sea water, is burned in an oxygen-containing inert gas flowing through a combustion tube which contains a catalyst and which is heated to a combustion supporting temperature. The amount of oxygen consumed is measured.

Inside the said combustion tube, down the gas stream from the catalyst, is provided a decomposing agent which consists of a hydroxide or carbonate of an alkali metal, or a hydroxide, oxide or carbonate of an alkaline earth metal, or of any mixture of them, thereby to decompose into sodium chloride and oxygen the sodium hypochlorite which was formed from the combustion of the test water.

7 Claims, 12 Drawing Figures

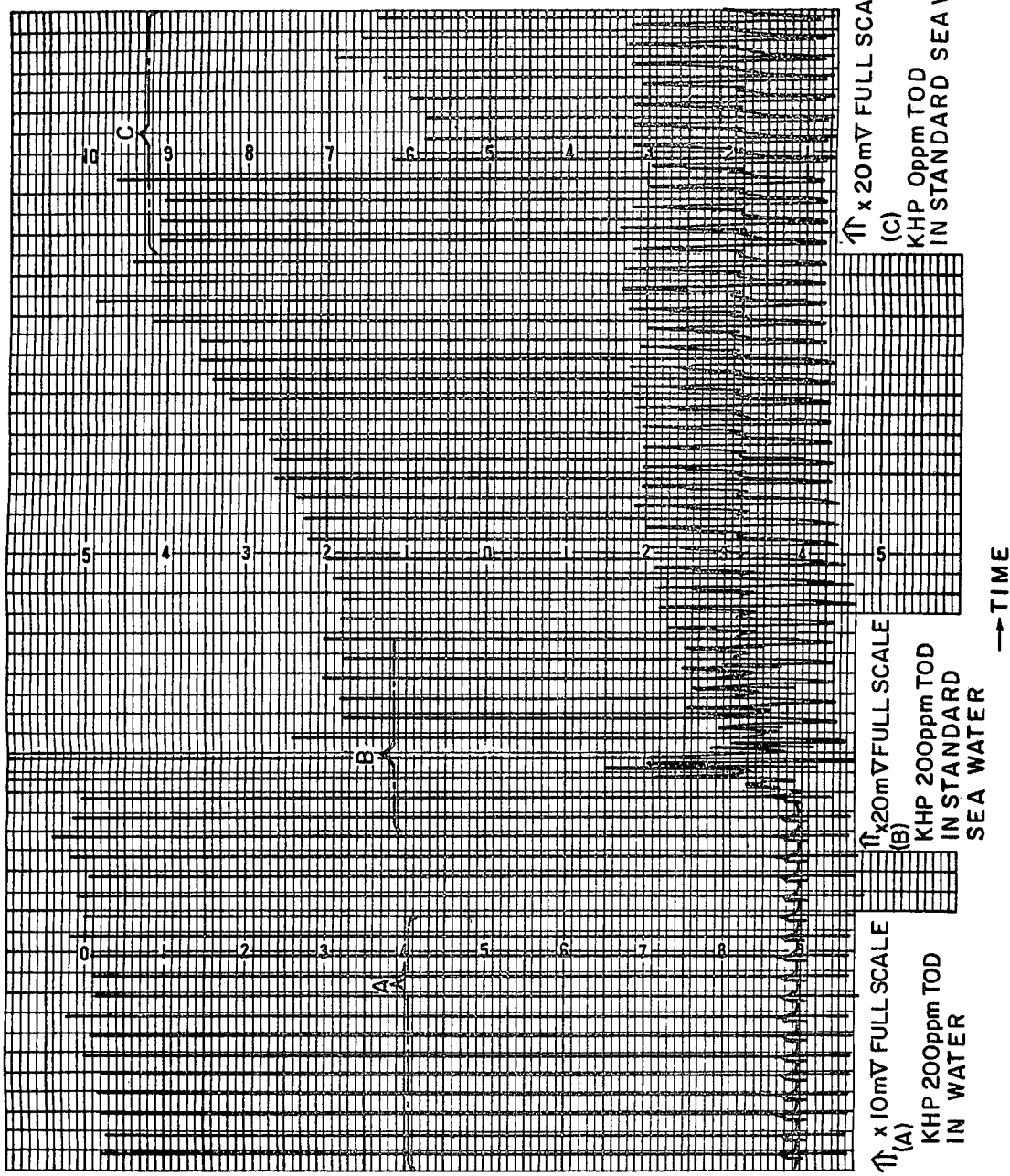

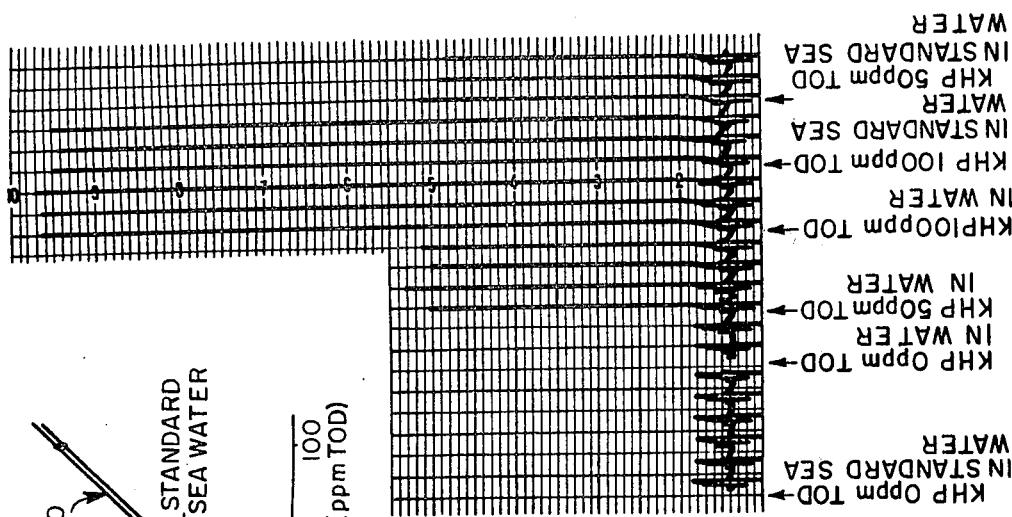
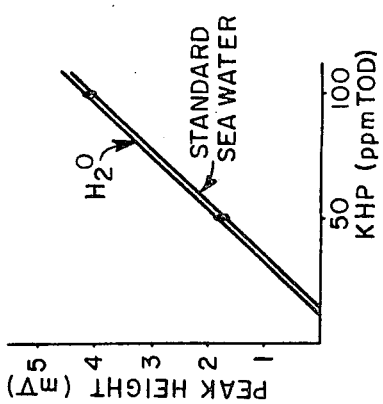
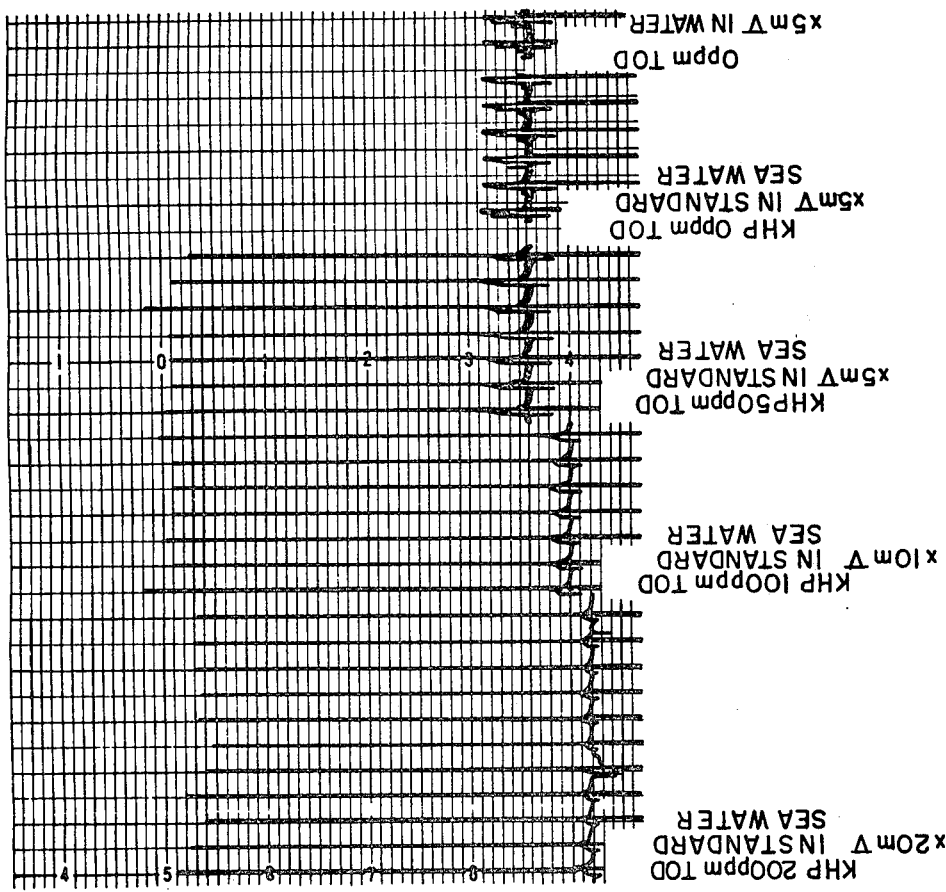

→TIME

→TIME

→TIME

METHOD AND APPARATUS FOR DETERMINING TOTAL OXYGEN DEMAND OF COMBUSTIBLE MATERIALS IN AQUEOUS DISPERSION

This is a continuation, of application Ser. No. 638,361, filed Dec. 8, 1975.

BACKGROUND OF THE INVENTION

In recent years, control of pollutants in waste water as a measure for prevention of water pollution is being envisaged in many countries. It is necessary, for that purpose, to establish a method for quickly determining the concentration of pollutants in water as well as for measuring the quantity of water. For the purpose of measuring the concentration of pollutants in water, great importance has been assumed by the TOD (total oxygen demand) analyzer as an apparatus for monitoring the quality of water. With such apparatus nearly all organic materials are 100 percent detected. Also, measurement is very quick.

The TOD analyzer referred to above has a structure of the type, for instance, described in U.S. Pat. No. 3,560,156. When, however, attempts are made to measure the TOD of sea water with the use of a TOD analyzer having such a structure, serious problems arise.

That is to say, when the combustion supporting temperature is above 800° C, fluctuations of the base line occur; and, at the same time, there is an increase in the so-called "blank value, " namely, the value measured when no combustible material is present in the test liquid.

In the measurement of, particularly, the TOD of a liquid of low concentration, such as the rather low range of tens of ppm, the values obtained vary widely and the reliability of the test is extremely low; it is virtually impossible to conduct an accurate measurement.

The above-mentioned phenomena are accounted for by the following facts:

While the melting point of sodium chloride is 800.4° C and its boiling point is 1413° C, it is of such a nature that, above its melting point, its vapor pressure is high and it sublimates. Therefore, sodium chloride contained in sea water is vaporized at a high temperature, and is oxidized by contact with the catalyst, thereby forming sodium hypochlorite and accordingly consuming oxygen in the feed gas which is intended for use in combustion of organic or other impurities.

Therefore, if the vapor pressure of the sodium chloride were to be lowered, the amount of sodium chloride oxidized by contact with the catalyst would decrease and, consequently, it should be possible to limit the fluctuation of the base line and the rise of the blank value. Accordingly, in the case of sea water, a method is used wherein the measurement is conducted at a lower temperature, for instance, 770° C.

It is true that, after the combustion temperature has been lowered, there is reduced formation of sodium hypochlorite, and the aforesaid problems are resolved to a certain degree. This method is subject, however, to a major drawback in that with the lowering of the combustion temperature, the rate of oxidization of organic materials decreases, and errors in the values obtained from the measurement become greater. From this reason, the combustion temperature is, in the method, set at 770° C, such being regarded as the temperature at which sodium hypochlorite is not likely to be formed as mentioned above, and yet, the temperature is still high enough that organic materials are easily oxidized.

As a consequence, in the foregoing method, the TOD of sea water is measured at 770° C and that of ordinary waste water is measured at 900° C. Accordingly, the method has a drawback in that, on account of the existence of this difference in temperature, it is impossible alternately to measure the TOD of sea water and that of ordinary waste water, or, even if it were at all possible, it would take a long time to stabilize the apparatus. The conventional method of measuring the TOD of sea water makes it a prerequisite, as heretofore mentioned, to prevent as far as practicable, the formation of sodium hypochlorite. As a natural consequence, the process of measurement becomes complex. Further, those components contained in sea water which are less combustible remain wholly or partially unburned. Hence errors arise in the values obtained from the measurements.

The present invention eliminates the shortcomings of the prior art, and one of its main objects is to conduct a measurement of the TOD of sea water at the same combustion temperature as with ordinary waste water, without experienceing undesirable fluctuations in the base line and in the blank values.

BRIEF DESCRIPTION OF THE DRAWINGS

FIGS. 3 and 7 are typical recorder charts obtained in conventional measurements of TOD of standard sea water.

FIGS. 4, 5, 8 and 10 are recorder charts obtained in measurements of TOD of standard sea water conducted in accordance with the method of the present invention.

FIG. 10 is a chart which shows values obtained on standard sea water tests utilizing one embodiment of this invention.

DESCRIPTION OF THE PREFERRED EMBODIMENTS

The term "combustible materials" as used in the present specification means materials which, when heated in the presence of a catalyst, react with oxygen and form oxides, that is to say, "combustion" occurs in the broad sense of the word. Further, the term "Total Oxygen Demand (TOD)" means the amount of oxygen that is required when combustible materials contained in water are caused to undergo "combustion" in the oxygen-containing feed gas, to convert the component elements of the combustible materials into stabilized forms of oxides.

The TOD analyzer is classified into two types as follows.

Figure 1A:
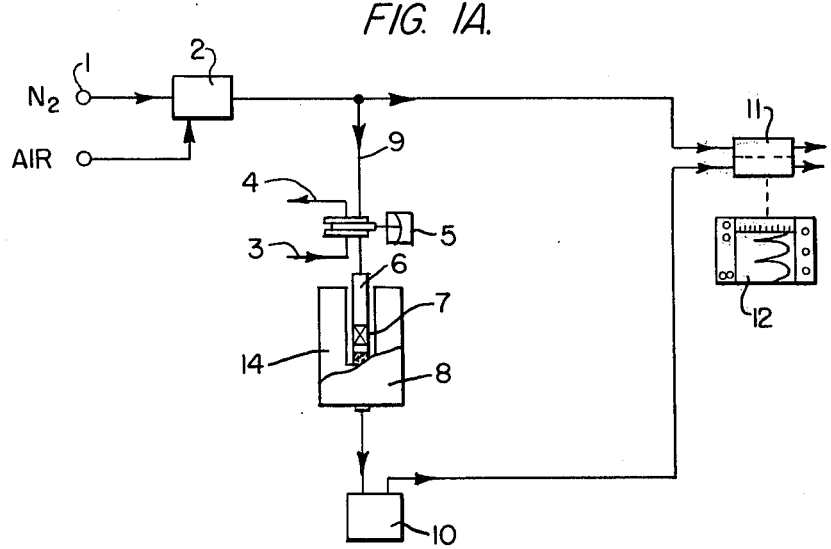
FIGS. 1-A and 1-B are diagrams which show schematically examples of an apparatus according to the present invention.
Figure 1B:
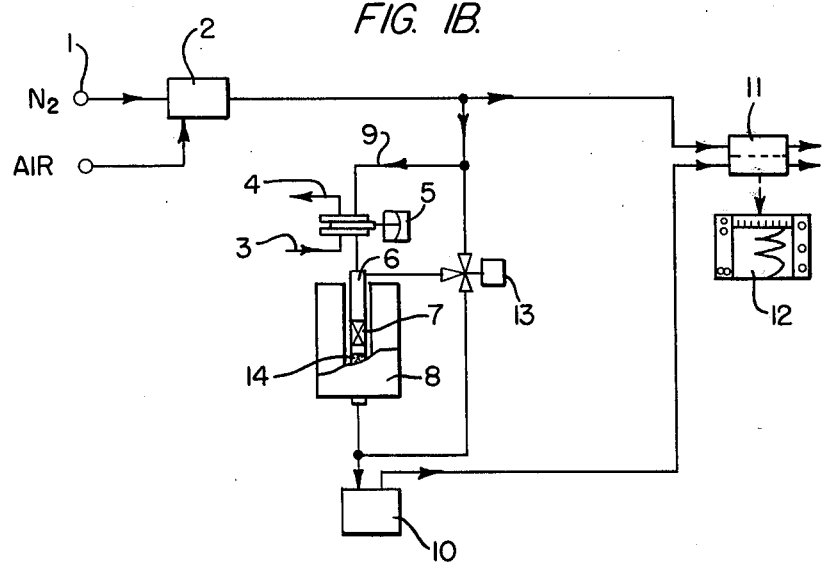

According to one type, test water is instantaneously poured into a feed gas which is running at a constant rate of flow, as is shown in FIG. 1, "A". In another type, test water is poured into the combustion tube and the flow rate of the feed gas for combustion is reduced to a remarkable degree for a certain time, thereby to prolong the time during which combustible materials are in contact with the catalyst so that the oxidation may be completed, and thereafter the flow rate of the gas is increased again and the portion of the gas in which oxygen has been consumed is rapidly transmitted to a detector, as shown in FIG. 1, "B".

In FIGS. 1-A and 1-B, the number 1 indicates a gas tank; 2 is a unit for controlling the concentration of oxygen in the feed gas; 3 is a test water inlet; 4 is a test water outlet; 5 is a device for pouring test water; 6 is a combustion tube; 7 is a catalyst bed; 8 is an electric furnace; 9 is tubing leading to pouring device 5; 10 is a dehumidifier; 11 is an oxygen detector of the solid electrolyte fuel cell type; and 12 is a recorder.

Referring to FIG. 1-B, 13 is a flow regulator and 14 is a decomposer bed.

In an apparatus as described above, test water, which is fed in from the test water inlet 3, is mixed with nitrogen gas which contains a certain fixed amount of oxygen and which flows through tubing 9. When the test water is poured into the combustion tube 6 which contains the catalyst and which is kept at a high temperature, combustible materials in the test water burn and each component element of the combustible materials becomes a stable oxide. As a result, the concentration of oxygen contained in the nitrogen gas decreases and the decrease is detected by the oxygen detector 11. The decrease in the concentration of oxygen is recorded as a peak by the recorder 12. The TOD value of test water is obtained by comparing the height of the peak, recorded as above, with the working curve which was obtained from the peak height of a standard solution having a known TOD value. The TOD value of the standard solution is obtained by calculating the amount of oxygen that is necessary for the compounds contained in the solution to be oxidized completely with C oxidized into $CO_2$, H into $H_2O$, N into NO, and S into $SO_2$.

It has been discovered that, with the measurement of the TOD of sea water, sodium chloride vapor is oxidized and sodium hypochlorite is formed. Hence, a portion of the oxygen provided in the feed gas for combustion, oxygen is consumed in this reaction. However, according to the present invention, the sodium hypochlorite which is formed is caused to pass through a decomposer bed whereby the formed sodium hypochlorite is reduced to sodium chloride with attendant liberation of oxygen. Therefore, the oxygen formed by this reduction step exactly compensates for the previous decrease of oxygen caused by the oxidation of sodium chloride. Accordingly, non-uniformity in the concentration of oxygen in the feed gas for combustion is virtually avoided, and it is thus possible to prevent fluctuations of the base line in the detector and of the blank value when there is no input.

To put it in other words, much significance lies in the present invention in the fact that oxygen consumed without serving to oxidize organic materials is again separated from the resulting oxides and re-introduced into the test stream. For that purpose, it is of importance that the means for decomposing sodium hypochloride is provided downstream of the zone where combustion takes place and upstream of the detector.

As a result of having examined various kinds of inorganic materials for use as decompsoing agents, it has been found that the hydroxides and carbonates of alkali metals, and the hydroxides, oxides and carbonates of alkaline earth metals, used either singly or as any mixtures thereof, or used with an inactive support, are very effective for the purpose.

By the term "inactive support" is meant a material which has nothing to do with the giving and taking of oxygen under the TOD analyzing conditions. Examples are quartz fibers, ceramic fibers, diatomaceous earth, etc.

The use of a single compound for decomposing agent may be exemplified by lumps of calcium oxide which are crushed and sieved to a uniform grain size so that a layer of such material has sufficiently high permeability to let the flow of feed gas through and to avoid excessive back pressure when test water is poured in, and when the sample to be analyzed evaporates.

To obtain reproducible results, the length of the decomposer bed must be at least one centimeter, but it is to be clearly understood that the length is not limited to such.

The following is an example of the use of selected members of the aforesaid group of compounds as a mixture. Soda lime is a white granular solid made by immersing quick lime in a thick solution of caustic soda and then heating it, and is a mixture of calcium oxide and sodium hydroxide. This may be used as a decomposing agent, as well.

In the case of a material which cannot be obtained in a suitable grain size, such material may be dissolved in water and an inactive support immersed in the solution. The support is removed and dried by evaporation, thereby causing the surface of the inactive support to be dressed with the decomposing agent. On the other hand, quartz fibers or the like may be sprinkled with such material in finely pulverized form. An inactive support thus covered with a decomposing agent is then fitted into the combustion tube, downstream of the combustion chamber.

When measuring the TOD of sea water, to restrain the fluctuation of the base line and the rise of the blank value, the position of the decomposer bed is also very important. That is to say, it is necessary that the decomposer bed be placed in such a position that it decomposes the sodium hypochlorite and gives rise to formation of oxygen, thereby to compensate for the previous decrease in the concentration of oxygen. It is surprising that this position is important, during the short time in which the feed gas moves forward with its oxygen-depleted portion resulting from the formation of sodium hypochlorite. It has been found that the degree to which the concentration of oxygen has decreased and the extent to which sodium hypochlorite has been formed are in nearly perfect agreement. If a lag is provided in the feed gas between the portion in which the concentration of oxygen has decreased and that in which hypochlorite exists, there occurs, as sodium hypochlorite decomposes and oxygen is generated in the decomposer bed, a portion in which the concentration of oxygen rather increases, and this gives rise to the occurrence of plus and minus peaks on the recorder chart, making the fluctuation of the base line much more complicated. Therefore, it is necessary to see to it that this is avoided.

One important factor contributing to the occurrence of a lag between the portion in which the concentration of oxygen has decreased and that in which sodium hypochlorite exists is thought to be as follows. Namely, when sea water is poured into the combustion tube, water vaporizes in an instant and the feed gas in the tube contains a large amount of steam. As the gas moves forward and enters the lower temperature zone, water that is in excess of the amount just sufficient to maintain the saturated vapor pressure condenses on the tube wall; and at this time, sodium hypochlorite is dissolved in water and is separated from the gas layer. Thereafter, only the portion in which the concentration of oxygen has decreased moves forward. Even if such a gas is passed through the decomposing agent, there is, in the gas, no sodium hypochlorite to be decomposed. Thus, as a natural consequence, the fluctuation of the base line and the rise of the blank value, such as are seen with the measurement of the TOD of sea water, are unavoidable.

In view of the above, the location at which the decomposer bed is to be provided is critical. The bed must be located downstream of the catalyst bed gas exit and separated from the catalyst bed. The tube or other passageway leading from the combustion bed to the decomposer bed must be positioned in a zone where there is substantially no condensation of water on the tube wall. The decomposing bed must be maintained at a temperature at which there is (a) substantially no decomposition of the decomposing agent itself; (b) insufficient fusion of the decomposing agent to cause closure of the passage of gas and the giving and taking of oxygen by the decomposer itself. With calcium oxide, for instance, a temperature in the range of 200° C to 600° C is suitable, and with soda lime, a temperature in the range of 80° C to 200° C is suitable.

If, furthermore, there is provided in between the catalyst and decomposer beds a space which has a temperature range that is required for the deposition of sodium chloride which sublimated at the combustion temperature, it serves to eliminate obstruction to the action of the decomposing agent and to prevent the closure of the gas passage and the rise in the flow resistance, thus making it possible to conduct the measurement of TOD continuously over a long period of time.

Figure 2:
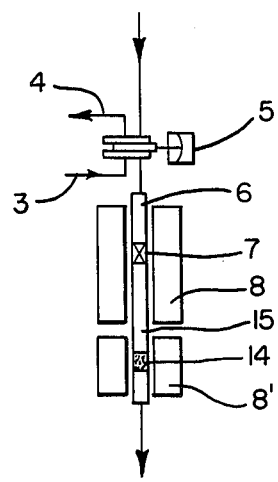
FIG. 2 shows schematically another apparatus according to the invention.

While, ordinarily, the decomposer bed 14 is provided at the aforesaid position downstream of the catalyst bed in the combustion tube as shown in FIGS. 1-A and 1-B, the apparatus may also be so arranged that, as shown in FIG. 2, another electric furnace 8' is provided downstream of the combustion tube from the catalyst bed 7, and arranged to heat the decomposer bed 14 to a predetermined fixed temperature at which the decomposition agent functions at peak efficiency. In this way, the effectiveness of the present invention becomes much greater. In this instance, it is necessary to maintain the temperature of the combustion tube 15, between the electric furnace 8 for heating the catalyst bed and the decomposer bed heater 8', at a temperature high enough to prevent condensation of water while permitting deposition of sodium chloride.

In an oxygen detector of the liquid fuel cell type, 20% KOH aqueous solution is used as electrolyte for the cell. There is provided, upstream of the fuel cell, a scrubber which contains 20% KOH aqueous solution, the same as the electrolytic solution, in order to prevent carbonic acid gas, etc., which may have been formed by the combustion, from reacting with the electrolytic solution, thereby causing changes in its concentration. It was thought that this scrubber might have, as its secondary function, an effect which is similar to that of the present invention, but, actually, it showed little such effect. It is thought that this is because there is, in the liquid phase reaction, a lack in power of decomposing sodium hypochlorite or a time lag in the generation of oxygen, though, to show such effect, there must be decomposition of sodium hypochlorite and generation of oxygen so as to compensate for the previous loss of oxygen in the portion of the feed gas in which reaction took place to form hypochlorite, as is clear from the foregoing explanations.

It has been discovered, furthermore, that an aqueous solution of 1 to 5 pct. calcium chloride shows the same behavior as sea water with respect to the measurement of TOD. As a result of the application of the present invention, an effect which is equal to that obtained in the case of sea water was recognized. The present invention is, therefore, particularly effective for the measurement of the TOD of waste water containing about 1 to 5 pct. of a halide of alkali metals or alkaline earth metals. However, it is to be clearly understood that the application of this invention is not limited to such.

It has been found that the effectiveness of the decomposition agent decreases in time with the deposition of sodium hypochlorite. Therefore, it is preferable to lower the combustion temperature and thus reduce the amount of sodium hypochlorite formed, thereby to maintain the effectiveness of the decomposition chemical for a longer period.

We will now explain the construction, action and novel effects achieved by the present invention, with reference to several examples which are not intended to limit the scope of the invention.

EXAMPLE 1

A test was conducted to determine the signals obtained when the TOD of sea water is measured with the use of a TOD analyzer constructed and arranged as shown in FIG. 1-B but without the decomposer bed 14. A chart as shown in FIG. 3 was obtained on the oxygen density meter. The sample used was standard sea water. The following is a detailed description of the test.

The sample was prepared by dissolving 2.7213 sodium chloride (NaCl), 0.8807 g. magnesium chloride ($MgCl_2$), 0.1658 g. magnesium sulfate ($MgSO_4$), 0.1260 g. calcium sulfate ($CaSO_4$), 0.0863 g. potassium sulfate ($K_2SO_4$), 0.0123 g. calcium carbonate ($CaCO_3$) and 0.0076 g. magnesium bromide ($MgBr_2$) in water, making the total weight 1.0 kg. For combustion, nitrogen gas containing 500 ppm of oxygen was fed at a flow rate of 120 ml/min. 20 $\mu l$ of sample was poured in at intervals of five minutes, and at every pouring, the flow rate of feed gas was lowered to 10 ml/min for 60 seconds. The combustion temperature was 880° C. The catalyst bed was composed of 5 g. of platinum wire crumpled into a ball and sandwiched between two lumps of quartz fibers, 1 g. each, and was fitted in the middle of the combustion tube 6 (made of quartz; I.D. 12 mm; length 47.5 cm).

In the first stage of the test, of which the record is shown in Chart portion (A) of FIG. 3, an aqueous solution of potassium hydrogen phthalate (KHP) 200 ppm TOD was poured; and it was confirmed that the TOD analyzer was performing its normal function. In the next stage, as recorded in Chart portion (B), the test was switched over to the pouring of standard sea water of KHP 200 ppm TOD. Thereupon the peak line was broken off. Therefore, an attenuation by one-half was made and the full scale was set at 20 mV. As, under this condition, pouring of the standard sea water sample was continued, there was seen a gradual rise in the base line and peak heights; and, at the same time, broad fluctuations of the base line, plus and minus, were observed after the appearances of peaks. The test was then switched over to the next stage, recorded in Chart portion (C), where standard sea water at KHP O ppm TOD was poured; and there were observed a very high blank value (approx. 8 mV) and, in this instance as well, broad fluctuations of the base line, plus and minus, after the appearances of peaks.

As is seen from the above-mentioned test, with the use of the prior art, the blank value is extremely high and there are also fluctuations of the base line, so that when a measurement is made of the TOD of a low-concentration sea water, the values obtained are extremely uncertain. Hence it was difficult to obtain reliable values.

Subsequently, the effect of the present invention was confirmed under the test conditions as described below.

Immediately after the aforesaid test, there was provided in the TOD analyzer, as is shown in FIG. 1-B, a decomposer bed 14, which was composed of 0.5 g. calcium oxide having a grain size of 16 to 28 mesh, sandwiched between lumps of quartz fibers, 7.5 cm downstream of the platinum catalyst bed 7 provided inside the combustion tube 6. When the platinum catalyst bed 7 was heated to 880° C, the temperature of the decomposed bed 14 stood at 580° C. Other test conditions remained the same as the test according to the conventional method, as described. The results obtained are shown in FIG. 4. Measurements were made of TOD's of standard sea water samples containing, respectively, 0, 50, 100 and 200 ppm KHP, as well as of that of distilled water containing no KHP.

As will be seen from FIG. 4, the base line is stabilized with the same sample, and, at the same time, there is a marked decrease in the blank value. Consequently, the concentration of oxygen is clearly shown even in the measurement of sea water with low concentration. That is to say, it is possible, according to the present invention, to measure correctly values of only the TOD of organic materials, and no errors occur, as are present in the prior art.

EXAMPLE 2

Under the same conditions with the embodiment of the present invention included in Example 1 above, an apparatus was used wherein, as is shown in FIG. 1-B, a decomposer bed 14 was provided downstream of the platinum catalyst bed 7 inside the combustion tube 6, and working curves were prepared. The result is shown in FIG. 5-A. While, in said Figure, the working curve of the standard sea water was slightly below that of water, it was proved, as is seen from FIG. 5-B, that there is no hindrance to the operation of measurement even if the measurement of the TOD of water is immediately followed by measurement of the TOD of sea water.

EXAMPLE 3

A measurement was conducted with the use of a TOD analyzer as shown in FIG. 1-A but without the decomposer bed 14. The combustion temperature was 900° C. A quartz tube (I.D. 12 mm; length 47.5 cm) was employed for the combustion tube; and in the middle of which, 10 g. of platinum wire, crumpled into a ball and sandwiched between layers of quartz fibers, 2 g. each, at the top and bottom, was fitted. The combustion gas used was a nitrogen gas containing 1.2% oxygen, and was fed at a flow rate of 150 ml/min. 20 $\mu$l each of the samples was poured. The record obtained with the pouring of an aqueous solution of KHP 200 ppm TOD is shown in FIG. 6.

Figure 7:
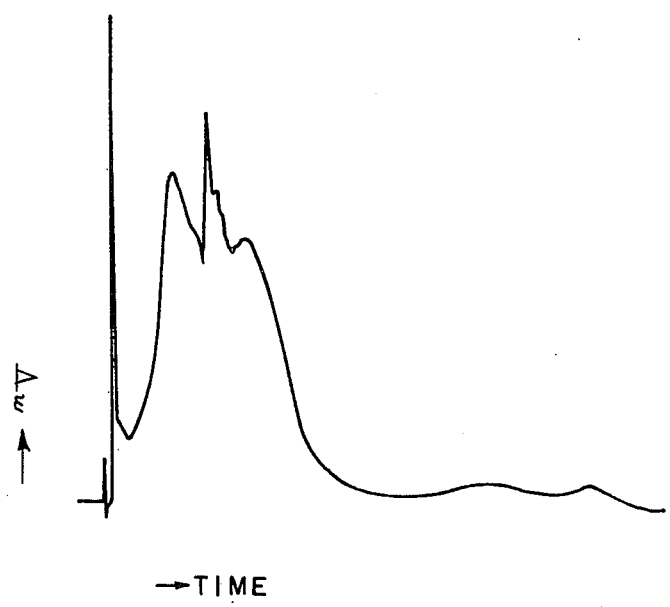

In FIG. 7 is shown the record which was obtained when, into the said apparatus, an aqueous solution of 5% calcium chloride containing KHP 200 ppm TOD was poured. After acute peaks, broad and high peaks appear.

In the next place, the combustion tube 6, as shown in FIG. 1-A was provided, 12 cm downstream of the catalyst bed 7, with a decomposer bed 14 which consisted of 3 g. of small-grain soda lime stuffed inside the tube and fixed with quartz fibers; and when the tube was heated to 900° C at the position of the catalyst bed 7, the temperature at the position of soda lime stood at 150° C. After stabilization of the condition of the apparatus, an aqueous solution of 5% calcium chloride containing KHP 200 ppm TOD was poured; the results are shown in FIG. 8.

Figure 6:
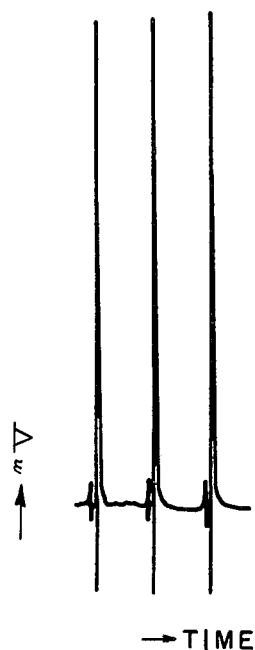
FIG. 6 is a recorder chart obtained in measurement of TOD of water carried out according to the conventional method.
Figure 8:
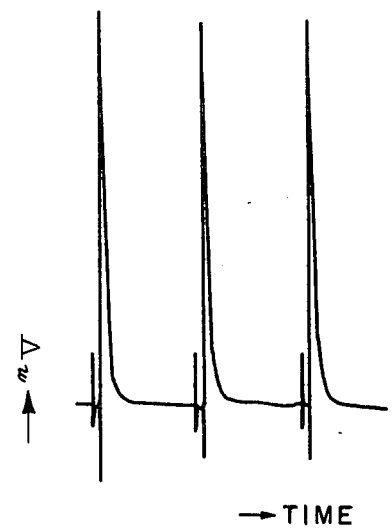

As will be seen from the comparison between FIGS. 6 to 8, while broad, obtuse peaks occur with the method according to the prior art, only acute peaks occur with the embodiment of the present invention, in which there are no broad, obtuse peaks at all. Thus, it is seen that the apparatus according to this invention works with sharp sensitivity.

EXAMPLE 4

Figure 9:
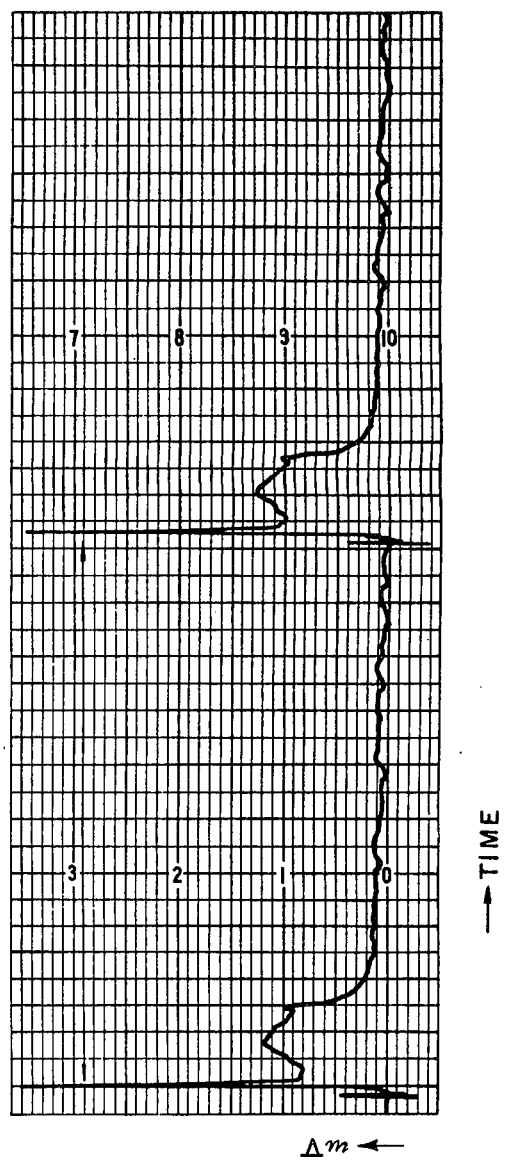
FIG. 9 is a chart which shows the action of a scrubber used with the liquid electrolyte fuel cell.

Under the same test conditions as in the case of the prior art included in Example 3 above, the dehumidifier 10 was removed and, instead, a scrubber, which is employed when the liquid electrolyte fuel cell is made use of, was provided between the combustion tube 6 and the oxygen detector 11, and into this scrubber was placed an aqueous solution of 20% caustic potash. After stabilization of the condition of the apparatus, an aqueous solution of 5% calcium chloride containing KHP 200 ppm TOD was poured, and as the result, a record as shown in FIG. 9 was obtained. As in the case of FIG. 6, broad, obtuse peaks appeared after acute peaks.

A further similar test was made. Though under the same test condition as in Example 1, the combustion tube 6 was provided with nothing but the platinum catalyst bed, and between the dehumidifier 10 and the oxygen detector 11 was provided a scrubber, made of steel (I.D. 10 mm; length 5 cm), filled with 1 g. of soda lime. Its effect was examined with pouring of standard sea water, but no effect was to be recognized.

Figure 10:
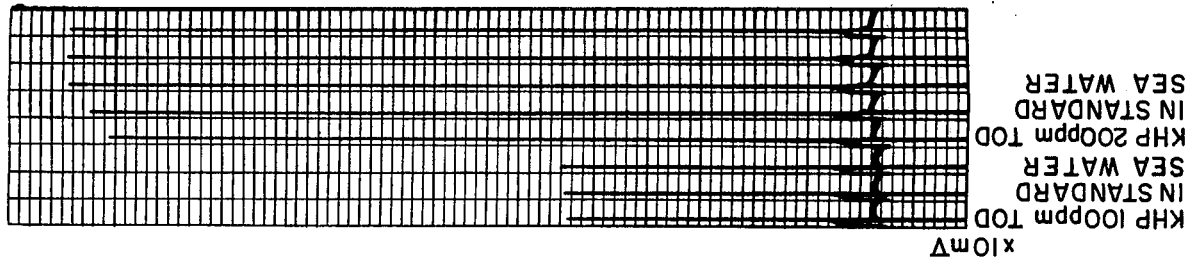

A still further test was made in this manner. Namely, while under the same test condition as in Example 1, the combustion tube 6 was provided, 7.5 cm downstream of gas from the platinum catalyst bed 7, with a decomposer bed 14 consisting of 0.5 g. of quartz fibers sprinkled with 0.1 g. pulverized magnesium oxide. When the tube was heated to 880° C at the position of the platinum catalyst bed 7, the temperature of the magnesium oxide layer which constituted the decomposer bed stood at 480° C. When standard sea water was poured into the apparatus thus prepared, the same record as in the case of water was obtained, as is shown in FIG. 10.

EXAMPLE 5

While under the same test conditions as in Example 1, the combustion tube 6 was provided, 12.5 cm downstream from the platinum catalyst bed 7, with a decomposer bed 14 consisting of 0.2 g. of granular caustic soda wrapped up in 1 g. of quartz fibers. When the platinum catalyst bed was heated to 880° C, this caustic soda layer, constituting the decomposer bed, was at a temperature of 150° C. When the TOD of standard sea water was measured with the apparatus so prepared, the caustic soda became fused in the course of measurement and adhered to the surfaces of the quartz fibers, but the record obtained was normal, and the apparatus proved effective for the decomposition of sodium hypochlorite.

EXAMPLE 6

While under the same test conditions as in Example 1, the combustion tube 6 was provided 7.5 cm downstream of the platinum catalyst bed 7, with a decomposer bed 14 consisting of 2 g. of sodium carbonate in granules, 16 to 28 mesh, fixed in form with 0.2 g. of quartz fibers. When the catalyst bed 7 was heated to 890° C, the temperature of the decomposer bed consisting of sodium carbonate stood at 565° C. When the TOD of the standard sea water was measured, no abnormal peaks nor increases in the blank value were observed.

EXAMPLE 7

While under the same test conditions as in Example 1, the combustion tube 6 was provided 7.5 cm downstream of the platinum catalyst bed 7, with a decomposer bed 14 consisting of 0.5 g. quartz fibers sprinkled with 0.1 g. of calcium carbonate, which was fixed in the tube with an additional amount of 0.1 g. of quartz fibers. When said catalyst bed 7 was heated to 900° C, the temperature of the decomposer bed consisting of calcium carbonate stood at 430° C. When the TOD of the standard sea water was measured with the use of this apparatus, no increases in the blank value nor broad, obtuse peaks were observed.

EXAMPLE 8

Though, in this instance, the apparatus was nearly the same as in Example 1, the combustion tube 6 was as shown in FIG. 2, somewhat longer; and there was provided apart from the electric furnace 8, another electric furnace 8' with which independent heating was done. In the combustion tube 6 was provided the same decomposer bed 14 as was used in Example 5. Using the apparatus thus prepared, the platinum catalyst bed 7 was heated to 880° C, the decomposer bed 14 to 150° C, and the TOD of the standard sea water was measured. While, in the course of measurement, caustic soda became fused and adhered to the surfaces of the quartz fibers, the record obtained was normal and the apparatus proved effective for the decomposition of sodium hypochlorite.

It is worth particular mention that an apparatus as shown in FIG. 2, provided with another electric furnace 8', apart from the electric furnace 8, to heat the decomposer bed 14 independently, permits heating of the decomposer bed 14 to the temperature at which it acts most effectively, thus making it possible to obtain a satisfactory result in the decomposition of sodium hypochlorite.

EXAMPLE 9

As is shown in FIG. 1-A, there was provided in the combustion tube 6, downstream of the catalyst bed 7, a decomposer bed 14 which consisted of 1.0 g. of calcium oxide, having a grain size of 16 to 28 mesh, held between layers of quartz fibers. For the combustion tube, a quartz tube, having an I.D. of 12 mm and a length of 50 cm. was employed. When the catalyst bed 7 was heated to 900° C with the electric furnace 8, the decomposer bed was being heated at 400° C by the temperature gradient at the lower end of the electric furnace.

An operation was begun of successively pouring, into said combustion tube, 20 μl of sea water at intervals of five minutes. From the third day of such operation, a decrease was observed in the effectiveness of the decomposer, and the fluctuations of the base line and increases in the blank value began to be observed. At the same time, there was observed a decrease in the flow rate of the feed gas for combustion.

In order to clarify the causes for such, therefore, the decomposer bed 14 was removed, and pouring of sea water into the combustion tube, successively at intervals of five minutes, was continued for a further five days, and then the combustion tube was taken out and a close observation was made. It was found, as a result, that there was an accumulation of a solid substance on the inner wall of the combustion tube, centering around the position where the decomposer bed had been provided and extending further downstream in particular, in the zone where the temperature range was 200° to 400° C. As the result of chemical analysis, this solid substance was found to be sodium chloride. Namely, it was found that when sea water is poured into the feed gas at a combustion temperature of 900° C, sodium chloride contained in it sublimates and flows, with the flowing gas, downstream of the catalyst bed, and is gradually deposited, by reason of the temperature gradient of the combustion tube, on the wall of the combustion tube in the lower-temperature zone. The temperature range in which such deposition occurs is about 400° C down to 200° C; and it is thought that, when there is a decomposer bed in such temperature zone, sodium chloride deposits on the surface of the decomposing agent, and that this offers an obstruction to the action of the decomposing agent and, at the same time, partly blocks the passage of gas, resulting in an increase of flow resistance.

FIG. 2 shows an example of the apparatus for practical application of the present invention.

In FIG. 2, an apparatus of such construction as will permit heating of the combustion tube unit with two electric furnaces is used, and electric furnaces 8 and 8' are provided. This apparatus was so arranged that, when the catalyst bed 7 is heated to 900° C and the decomposer bed 14 to 400° C, the temperature of the combustion tube unit between said two electric furnaces falls in the range of 150° C to 250° C; and the aforesaid calcium oxide was used as decomposing agent. With this apparatus, an operation of pouring sea water at intervals of five minutes was continued for ten days, and there was no problem at all. After completion of the operation, the combustion tube was taken off and the tube wall was examined to observe any accumulation of sodium chloride. The largest accumulation was seen in that part of the tube which corresponds to the lower part of the electric furnace 8 where the temperature is in the range of 400° C down to 200° C.

Thus, it was found that if there is provided, between the catalyst bed and the decomposer bed, a space having a temperature range that is necessary for the deposition of sodium chloride, it is possible to continue measurement over a long period of time.

With the use of such decomposing agent as soda lime, which works effectively at a temperature in the range of 80° to 200° C, it is possible to do away with the electric furnace 8' and yet to maintain a proper temperature by utilization of the remaining heat of the electric furnace 8. There is produced in the combustion tube a temperature gradient of 900° C down to 200° C, and, as a matter of course, there occurs deposition of sodium chloride.

Although this invention has been described with reference to specific forms thereof, and although specific variations have been shown in the apparatus and the manner of performance of the steps of the method of this invention, it will be appreciated that other variations may be made without departing from the spirit and scope of this invention. For example, parts may be reversed, certain features may be used independently of other features, and equivalents may be substituted for specific elements that are shown in the drawings and described in the specification herein, all without departing from the spirit and scope of the invention as defined in the appended claims.

What is claimed is:

1. A method for measuring the total oxygen demand of a combustible material in an aqueous dispersion containing halide of alkali metals or alkaline earth metals which comprises:
    (a) flowing a feed gas stream of an inert gas containing oxygen at an essentially constant rate through a combustion conduit heated at a combustion supporting temperature and within the combustion conduit, flowing the feed gas stream through a combustion catalyst bed,
    (b) flowing the effluent gas from the catalyst bed into a decomposing bed containing a decomposing agent heated at a temperature to decompose sodium hypochlorite or hydrogen hypochlorite substantially instantly by action of the decomposing agent,
    (c) flowing the effluent gas from the decomposing agent bed into a continuous quantitative detector for gaseous oxygen to produce an electric signal which varies with the oxygen content of the effluent gas, and
    (d) while continuing the above procedure, injecting a small amount of an aqueous dispersion containing combustible material into the combustion conduit upstream from the catalyst bed whereby an electrical signal correlative with the total oxygen demand of an aqueous dispersion is produced.

2. A method as described in claim 1, wherein said decomposing agent is a compound selected from the group consisting of alkali metal hydroxides and carbonates, and alkaline earth metal hydroxides, oxides and carbonates.

3. A method as described in claim 1, wherein said decomposing agent is a mixture selected from the group consisting of alkali metal hydroxides and carbonates, and alkaline earth metal hydroxides, oxides and carbonates.

4. A method as described in claim 1, wherein said decomposing agent is supported on a material selected from the group consisting of quartz fibers, ceramic fibers and granular diatomaceous earth.

5. An apparatus for measuring the total oxygen demand of combustible materials in an aqueous dispersion containing halide of alkali metals or alkaline earth metals which comprises:
    (a) means for supplying a feed gas stream of an inert gas containing oxygen,
    (b) a combustion conduit having an inlet connected to means (a), and an outlet, said combustion conduit including a combustion catalyst bed with means for heating the contents thereof,
    (c) a decomposing agent bed provided in said combustion conduit downstream of said combustion catalyst bed, and
    (d) oxygen detecting means connected downstream of the combustion conduit and adapted to generate an electrical signal corresponding to the oxygen contained in the feed gas stream.

6. An apparatus as described in claim 5, wherein said means for heating the combustion catlayst bed and said means for heating the decomposing agent bed are separate.

7. An apparatus as described in claim 5, wherein said conduit includes a depositing zone for depositing sodium chloride sublimed at combustion supporting temperature, and is located between the catalytic bed and the decomposing agent bed in said combustion conduit.

* * * * *